(12) United States Patent
Adams et al.

(10) Patent No.: US 6,787,553 B2
(45) Date of Patent: Sep. 7, 2004

(54) METHODS FOR REMODELING NEURONAL AND CARDIOVASCULAR PATHWAYS

(75) Inventors: Michael A. Adams, Kingston (CA); Jeremy P. W. Heaton, Gananoque (CA)

(73) Assignee: Cellegy Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/192,281

(22) Filed: Jul. 9, 2002

(65) Prior Publication Data

US 2003/0008020 A1 Jan. 9, 2003

Related U.S. Application Data

(60) Continuation of application No. 09/902,787, filed on Jul. 12, 2001, now Pat. No. 6,458,797, which is a division of application No. 09/382,749, filed on Aug. 25, 1999, now Pat. No. 6,284,763.
(60) Provisional application No. 60/098,178, filed on Aug. 26, 1998.

(51) Int. Cl.[7] ................. A61K 31/519; A61K 31/40; A61K 31/135
(52) U.S. Cl. ................. 514/258.1; 514/423; 514/653
(58) Field of Search ................. 514/258.1, 423, 514/653, 258

(56) References Cited

U.S. PATENT DOCUMENTS

| | | | |
|---|---|---|---|
| 5,658,936 A | 8/1997 | Kifor et al. | |
| 5,688,499 A | 11/1997 | Banting et al. | |
| 5,770,606 A | 6/1998 | El-Rashidy et al. | |
| 6,284,763 B1 * | 9/2001 | Adams et al. | 514/248 |
| 6,458,797 B1 * | 10/2002 | Adams et al. | 514/252.16 |

FOREIGN PATENT DOCUMENTS

| | | |
|---|---|---|
| WO | WO 96/28142 | 9/1996 |
| WO | WO 97/33608 | 9/1997 |
| WO | WO 98/58633 | 12/1998 |
| WO | WO 00/12110 | 3/2000 |

OTHER PUBLICATIONS

Adams, M.A. et al. "Vascular control mechanisms in penile erection: phylogeny and the inevitability of multiple and overlapping systems." *International Journal of Impotence Research*, vol. 9, 1997, pp. 85–91.

Adams, M.A., et al., "Enalapril can prevent vascular amplifier development in spontaneously hypertensive rats." *Journal of Hypertension*, vol. 16, No. 3, pp. 252–260 (1990).

Adams, M.A., et al., "Evidence in vivo for induction of cardiovascular growth processes by vasoconstrictor systems." *Blood Pressure*, vol. 4, (Suppl 2), pp. 61–67 (1995).

(List continued on next page.)

Primary Examiner—Raymond J. Henley, III
(74) Attorney, Agent, or Firm—Townsend and Townsend and Crew LLP (57) ABSTRACT

The present invention provides a method of administration of an agent which acts to remodel neuronal or vascular pathways for the long term management of sexual dysfunction in both males and females. In a preferred embodiment, the invention provides a method of ameliorating or reversing pathogenic vascular degradative modeling in the ilio-hypogastric-pudendal arterial bed and genitalia comprising administering to a human patient in need of such treatment a therapeutically effective amount of an anti-pressor agent. The anti-pressor agent comprises one or more compounds selected from the therapeutic classes of direct vasodilators such as hydralazine and NO donors, ACE inhibitors, angiotensin-II receptor antagonists, $\alpha_1$-adrenergic receptor antagonists, $\beta$-adrenergic receptor antagonists, calcium channel blockers, and phosphodiesterase inhibitors. The anti-pressor agent may be co-administered with a diuretic compound, and is administered either chronically at low dose, or for short periods of time at doses higher than are typically used for the treatment of hypertension. In certain embodiments of the method of the invention, the anti-pressor agent is co-administered with a diuretic agent and/or prostaglandin-$E_1$.

33 Claims, 6 Drawing Sheets-

OTHER PUBLICATIONS

Adams, M.A., et al. "Common features regulating the systemic circulation and the penile vasculature," *Erectile Dysfunction*. pp. 27–38. London: Martin Dunitz Ltd. 1998.

Banting, J.D., et al., "Blunted cardiovascular growth induction during prolonged nitric oxide synthase blockade." *Hypertension*, vol. 30, No. 3, Part 1, pp. 416–421 (1997).

Childs, T.J., et al., "Regression of cardiac hypertrophy in spontaneously hypertensive rats by enalapril and the expression of contractile proteins," *Hypertension*, vol. 16, No. 6, pp. 662–668 (1990).

Christensen, K.L., et al., "Development of blood pressure in spontaneously hypertensive rats after withdrawal of long–term treatment related to vascular structure." *Hypertension*, vol. 7, No. 2, pp. 83–90 (1989).

Dukacz, S.A.W., et al., "The persistent effect of long–term enalapril on pressure natriuresis in spontaneously hypertensive rats." *American Journal of Physiology*, vol. 273, pp. F104–F112 (1997).

Friberg, P., et al., "Cardiac and vascular structural adaption in experimental hypertension." *European Heart Journal*, vol. 11, (Supplement G), pp. 65–71 (1990).

Gohike, P., et al., "Cardiac and vascular effects of chronic angiotensin converting enzyme inhibition at subantihypertensive doses." *Journal of Hypertension*, vol. 10 (Supplement 6), pp. S141–S144 (1992).

Harrap, S.B., et al., Proceedings of the HBPRCA. Transplantation studies of the role of the kidney in long–term blood pressure reduction following brief ACE Inhibitor treatment in young spontaneously hypertensive rats. *Clinical and Experimental Pharmacology and Physiology*, vol. 21, 129–131 (1994).

Jespersen, L.T., et al., "Cardiac mass and peripheral vascular structure in hydralazine–treated spontaneously hypertensive rats." *Hypertension*, vol. 7, No. 5, pp. 734–741 (1985).

Kett, M.M., et al., "Enalapril does not prevent renal arterial hypertrophy in spontaneously hypertensive rats." *Hypertension*, vol. 25, No. 3, pp. 335–342 (1995).

Lee, R.M.K.W., et al., "Debate: vascular remodeling." *Journal of Hypertension*, vol. 15, pp. 333–337 (1997).

Lundle, M.J., et al., "Long–term inhibition of the renin–angiotensin system in genetic hypertension: analysis of the impact of blood pressure and cardiovascular structural changes," *Journal of Hypertension*, vol. 15., No. 4, pp. 339–348 (1997).

Moreau, P., et al., "Angiotensin II increases tissue endothelin and induces vascular hypertrophy. Reversal by ET,—receptor antagonist." *Circulation*, vol. 96, No. 5, pp. 1593–1597 (1997).

Morton, J.J., et al., "Angiotensin II receptor antagonist losartan has persistent effects on blood pressure in the young spontaneously hypertensive rat: lack of relation to vascular structure." *Journal of Vascular Research*, vol. 29 pp. 264–269 (1992).

Nyborg, N.C.B., et al., "Lack of effect of anti–hypertensive treatment with felodipine on cardiovascular structure of young spontaneously hypertensive rats." *Cardiovascular Research*, vol. 19, pp. 528–536 (1985).

Okabe, H., et al. "The penis is not protected—in hypertension there are vascular changes in the penis which are similar to those in other vascular beds." *International Journal of Impotence Research*, vol. 11, 1999, pp. 133–140.

Rizzoni, D., et al., "Effects of losartan and analapril on small artery structure in hypertensive rats." *Hypertension*, vol. 32, pp. 305–310 (1998).

Sano T., et al., "Differential structural responses of small resistance vessels to antihypertensive therapy." *Circulation*, vol. 75, No. 3, pp. 618–626 (1987).

Sharti, M., et al., "Remodeling of myocardium and arteries by chronic anglotensin converting enzyme inhibition in hypertensive patients." Abstract, *Journal of Hypertension*, vol. 12, Suppl 4, pp. S37–S42 (1994).

Thybo, N.K. et al., "Dose–dependent effects of perindopril on blood pressure and small–artery structure." *Hypertension*, vol. 23, No. 5, pp. 659–666 (1994).

Wahlander, H., et a., "Therapeutic, but not low–dose, angiotensin–converting enzyme inhibition causes regression of cardiovascular changes in spontaneously hypertensive rats." *Journal of Cardiovascular Pharmacology*, vol. 27, pp. 327–334 (1996).

Weiss, L., "Long–term treatment with antihypertensive drugs in spontaneously hypertensive rats (SHR). Effects on blood pressure, survival rate and cardiovascular design," *Acta. Physiol. Scand.*, vol. 91, pp. 393–408 (1974).

* cited by examiner

METHODS FOR REMODELING NEURONAL AND CARDIOVASCULAR PATHWAYS

CROSS-REFERENCE TO RELATED APPLICATIONS

This application is a continuation of U.S. application Ser. No. 09/902,787, filed Jul. 12, 2001, now U.S. Pat. No. 6,458,797, which application is a divisional of U.S. application Ser. No. 09/382,74, filed Aug. 25, 1999, now U.S. Pat. No. 6,284,763, and which application claims to U.S. Provisional Application No. 60/098,178, filed Aug. 26, 1998. All the foregoing applications are incorporated herein by reference in their entirety.

TECHNICAL FIELD

The present invention relates to medical methods of treatment, pharmaceutical compositions, and use of antipressor agents to manufacture such pharmaceutical compositions. More particularly, the present invention concerns the administration of an agent which acts to remodel neuronal or vascular pathways for the long term management of sexual dysfunction in both males and females.

BACKGROUND OF THE INVENTION

The physiology of an erection or sexual arousal in both the male and female involves central nervous system initiation, neural pathway activation, and vascular smooth muscle relaxation. This signaling mediates vasodilation of the penile, clitoral labial, and vaginal arterial blood vessels and the trabecular meshwork of smooth muscle. The resulting decrease in vascular resistance promotes an increase in arterial inflow and the filling of the corpora cavernosa in the penis and clitoris. Subsequent to there being an appropriate high rate of inflow, the cavernosal "filling" results in occlusion of the sub-tunical veins and full rigidity. The rate of inflow is critical because if there is not enough volume change, venous occlusion can not take place. A selective structurally-based increase in penile resistance produces a substantial impediment to inflow. That is, if penile or clitoral vascular structure, or the vascular structure immediately "up-stream" from the genitalia, is more constrained than the rest of the circulation, there would be a "mismatching" of perfusion pressure and selective resistance, i.e. genital arterial insufficiency. On the other hand, it is likely that when hypertension is first established and there is a generalized up-regulation of structurally-based vascular resistance in all vessels, there would not be any deleterious effect on erectile function because of a "matching" between perfusion pressure and resistance. That is, despite the hypertrophy of the penile vasculature, the arterial pressure is proportionally elevated thereby allowing for adequate blood flow to the penis.

Pathological changes in the genital vasculature and alterations in function control systems have been shown to have a deleterious impact on erectile dysfunction. Local factors such as endothelin and sympathetic nerve mediated release of catecholamines have been shown to be important players in detumescence, but they also are likely to increase trophic responses in this tissue. The physiology of penile and clitoral erection and the structural maintenance of the tissue depends upon a balance between control systems that involve endothelial cells, vascular smooth muscle cells, fibroblasts, extracellular matrix, and nerves. Any shift in the balance of these control systems to either towards trophic responses such as vascular hypertrophy, focal fibrosis, or generalized production of the extracellular matrix or to the extremes of functional control systems can result in erectile dysfunction. Further, as structure and function are so closely related, it is becoming increasingly important in understanding the mechanisms of erectile dysfunction that we investigate the reciprocal impact of structural changes on function and of changes in functional control systems on structure.

The clitoris is the homologue of the penis, arising from the embryological genital tubercle. As a result, the two organs have similar structural and arousal response mechanisms. The clitoris consists of a cylindrical, erectile organ composed of three parts: the outermost glans or head, the middle corpus or body, and the innermost crura. The body of the clitoris consists of paired corpora cavernosa of about 2.5 cm in length and lacks a corpus spongiosum. During sexual arousal, blood flow to the corpora cavernosa of the clitoris cause their enlargement and tumescence.

The clitoris plays a major role during sexual activity in that it contributes to local autonomic and somatic changes causing vaginal vasocongestion, engorgement, and subsequent effects, lubricating the introital canal making the sexual act easier, more comfortable, and more pleasurable.

Vaginal wall engorgement enables a process of plasma transduction to occur, allowing a flow through the epithelium and onto the vaginal surface. Plasma transduction results from the rising pressure in the vaginal capillary bed during the sexual arousal state. In addition, there is an increase in vaginal length and lumenal diameter, especially in the distal 2/3 of the vaginal canal.

It has been well established that the generation of a penile and clitoral erections and vaginal and labial engorgement are greatly dependent on adequate blood flow to vascular beds which feed these organs. Both smooth muscle relaxation of the corpora cavernosa as well as the vasodilation of genital arterial vessels mediate the physiological response. One of the major fundamental etiologies of erectile dysfunction is, thus, inadequate genital arterial inflow. If there is an inappropriate structural narrowing in the supporting vasculature that is not associated with an increase in perfusion pressure, the blood flow into the organs at maximum dilation may be reduced and therefore be insufficient for the generation of an erection. There is increasing recognition that erectile dysfunction, although associated with, may appear prior to the onset of clinical signs of cardiovascular disease and therefore may be an early harbinger of progressing changes.

In both the male and female human, the aorta bifurcates on the fourth lumbar vertebra into the common iliac arteries. The common iliac arteries pass laterally, behind the common iliac veins, to the pelvic brim. At the lower border of the fifth lumbar vertebra, the common iliac arteries divide into internal and external branches. The internal iliac artery supplies blood to all of the organs within the pelvis and send branches through the greater sciatic notch to supply the gluteal muscles and perineum. After passing over the pelvic brim, the internal iliac artery divides into anterior and posterior trunks.

The anterior trunk of the internal iliac artery branches into the superior vesical artery, the inferior vesical artery, the middle rectal artery, the uterine artery, the obturator artery, the internal pudendal artery, and the inferior gluteal artery. The internal pudendal artery supplies blood to the perineum. The artery passes out of the pelvis around the spine of the ischium and back on the inside surface of the ischeal tuberosity and inferior ramus to lie in the pudendal canal. The branches from the internal pudendal artery are the inferior rectal artery which supplies the anal sphincter, skin and lower rectum; the perineal artery which supplies the scrotum in the male and the labia in the female; the artery of the bulb which supplies erectile tissue, the deep dorsal arteries of the penis or deep artery of the clitoris.

It has been demonstrated in several forms of experimental hypertension that "slow pressor mechanisms" such as hypertrophic structural changes in the vasculature can almost completely account for the long-term resistance changes associated with the elevated arterial pressure. Based on Poiseuille's law, it has been shown that vascular resistance in an intact vascular bed is a function of the overall hemodynamic effect of all lumen radii, the number of blood vessels, the length of the vessels and the blood viscosity. In hypertension, increased vascular resistance is most potently conferred by a structurally-based decrease in the radius of the lumen of arterioles and small arteries and also potentially by arteriolar rarefaction whereby even a small change in the average arteriolar radii throughout a vascular bed has a dramatic influence on the resistance to flow. Further, it has been demonstrated that such structural changes can precede the onset of hypertension and therefore may be an initiating mechanism.

Vascular beds in which there is chronic diminished blood flow suffer a degree of pathogenic vascular degradative modeling over time in response to static or circulatory hypoxia. That is, as a normal reaction to diminished blood flow, the lumen in these arteries diminishes in diameter over time, causing decreased blood flow and/or higher pressure during periods of peak blood flow. Those portions of the ilio-hypogastric-pudendal arterial bed which directly feed blood to the sex organs are examples of such less frequently used arterial beds. Because incidents of major blood inflow to the sexual organs are less frequent than to most other organs, a gradual hypoxic response is seen over time in the vasculature directly feeding these organs and in the organs themselves. The body has a self-regulating mechanism to combat this pathogenic modeling: it is known, for example, that in the human male there are a number of spontaneous nocturnal erections which occur as a result of the body's mechanism for combating hypoxia in penile tissue. Nevertheless, the arteries in a normal flaccid penis and the un-enlarged clitoris and labia are constricted. As a result, typical oxygen concentrations in such tissues are closer to venous rather than arterial oxygen levels. Periodic vasodilation of the penis and clitoris increases oxygen levels in these tissues. The higher oxygen levels supplied to tissue in the penis and clitoris, as well as vasodilation itself, shut down adverse metabolic processes such as TGF-b production and pathogenic vascular wall modeling which result in long term tissue damage.

Therefore, it is differential changes in genital vascular resistance that is likely to be a critical issue in erectile function. That is, if such vascular structural changes take place in the genitalia in the absence of hypertension or systemic changes in vessel structure there would not be the increase in arterial pressure required to compensate for the increased resistance. It may be that this condition could occur as an early indicator of progressing cardiovascular disease. The appearance of erectile dysfunction preceding the global clinical signs of hypertension may, in fact, suggest an increased susceptibility of this vascular bed to pathological changes.

SUMMARY OF THE INVENTION

In its principal embodiment, the present invention provides a method for the long term management of sexual dysfunction in males and females by administering a therapeutic agent which remodels neuronal or vascular pathways. In a preferred embodiment, the invention provides a method of ameliorating, inhibiting or reversing pathogenic vascular degradative modeling in the ilio-hypogastric-pudendal arterial bed and genitalia comprising administering to a human patient in need of such treatment a therapeutically effective amount of an anti-pressor agent. In one embodiment, the present invention provides the use of an anti-pressor agent for the manufacture of pharmaceutical compositions for ameliorating, inhibiting or reversing pathogenic vascular degradative modeling in the ilio-hypogastric-pudendal arterial bed and genitalia.

The anti-pressor agent is administered chronically at low doses ranging between about one-twentieth to about one-half the dose required to evoke vasodilation in a patient exhibiting normal circulation or, alternatively, is administered over a period of time ranging between about five days to about 21 days at higher doses ranging between about 1.5 to about 3 times the dose required to evoke vasodilation in a patient exhibiting normal circulation.

BRIEF DESCRIPTION OF THE DRAWING FIGURES

In the Drawing:

FIGS. 2a and 2b represent, respectively, the curves for administration to the penile vascular beds of the SHR and SD rat strains. FIGS. 2c and 2d represent, respectively, the curves for administration to the hindlimb vascular beds of the SHR and SD rat strains.

DETAILED DESCRIPTION

The present invention contemplates the use of anti-pressor agents to remodel vasculature in the arterial beds supplying blood to the sex organs, and in the vascularity of the sex organs themselves. There has been some controversy in the literature as to the correct definition of the term "vascular remodeling," as evidenced by the exchange of letters in the *Journal of Hypertension*, 15: 333–337 (1997). The controversy in the nomenclature centers, in part, around the use of the terms "hypotrophic," "eutrophic," and "hypertrophic" as modifiers for the term "remodeling" as well as the use of the prefix "re-" in the word "remodeling."

The "trophic" terms have been objected to because of their suggestion that some sort of growth change accompanies the observed vascular changes. The term "remodeling" was initially applied in the literature to the observation in spontaneously hypertensive rats and in hypertensive humans that the interior lumen radius ($r_1$) of blood vessels was greatly diminished while vessel wall mass (w) remained constant. The result was an observed increase in the ratio of $w/r_1$ which correlated with blood pressure elevation. The term "remodeling" was applied to the observed phenomenon, primarily because of the surprising consistency in total wall mass. It was thought that some sort of remodeling of the internal cellular structure of the blood vessel had occurred which permitted a change in lumen radius without a corresponding change in vessel wall mass.

The "re-" prefix has been objected to mainly because of the suggestion that some sort of "modeling" of the vasculature has already occurred, and subsequent changes (for good or ill) result in a "re-"modeling of those changes.

Lacking a general consensus of the term "vascular remodeling" in the medical community, the term "pathogenic vascular degradative modeling" will be applied, throughout this specification and the appended claims, to denote the pathogenic or degradative increase in the ratio $w/r_1$ of vasculature, irrespective of the cause. The term "vascular remodeling" as used throughout this specification and the appended claims will mean the amelioration, inhibition or reversal of pathogenic vascular degradative modeling; that is the amelioration, inhibition or reversal of the increase in the ratio of vascular $w/r_1$.

The term "anti-pressor agent" as used herein denotes a therapeutic agent which acts either directly or indirectly to lower blood pressure. The term anti-pressor agent is chosen, rather than the more specific term "antihypertensive" agent, because the invention contemplates the use of agents which are effective to increase vascular flow in both hypertensive and normotensive patients. Anti-pressor agents contemplated for use in the method of the present invention include agents which act to bring about a lowering of blood pressure by any of a number of different physiological mechanisms. Anti-pressor agents include compounds belonging to a number of therapeutic classes based upon their mechanism of action, even though the therapeutic outcome is the same. Anti-pressor agents suitable for the method of this invention include compounds which are direct-acting vasodilators such as NO donors and hydralazine. Other suitable anti-pressor agents are compounds which act to inhibit the enzyme which converts the less potent decapeptide vasoconstrictor, angiotensin-I, to the more potent octapeptide vasoconstrictor, angiotensin II (so-called angiotensin-II converting enzyme inhibitors or "ACE inhibitors"), as well as agents which block the binding of angiotensin-II to the $AT_1$ receptor ("angiotensin-II receptor antagonists"). Anti-pressor agents useful in the method of the present invention also include vasodilating agents which act at $\alpha_1$-adrenergic receptors or β-adrenergic receptors in the smooth muscle of vascular walls ("$\alpha_1$-adrenergic receptor antagonists" and "β-adrenergic receptor antagonists"), as well as agents which act to decrease intracellular calcium ion concentration in arterial smooth muscle ("calcium channel blockers"). Suitable anti-pressor agents for use in the present invention also include activators of the enzymes guanylyl cyclase and adenyl cyclase such as YC-1 and forskolin, respectively. $PGE_1$ (prostaglandin-$E_1$), which acts both as an anti-pressor agent and as a sexual response initiator, is also suitable for use in the invention. Also contemplated as falling within the scope of the invention for use as anti-pressor agents are phosphodiesterase inhibiting agents, particularly type-3 and type-5 phosphodiesterase inhibitors. Antagonists of PDE-5 (phosphodiesterase type 5), the enzyme primarily responsible for the degradation of cyclic guanosine monophosphate (cGMP), produce an increase in levels of cGMP, which, by way of "cross-talk," also decreases the activity of PDE-3, the enzyme primarily responsible for the degradation of cyclic adenosine monophosphate (cAMP). Thus, increasing levels of cGMP acts to inhibit the PDE-3 enzyme, thereby blocking the degradation of cAMP and causing an increase in cAMP levels. Thus, inhibition of either PDE-5 or PDE-3 results in an overall increase in concentrations of cAMP and cGMP.

Specific examples of NO donors include glyceryl trinitrate, isosorbide 5-mononitrate, isosorbide dinitrate, pentaerythritol tetranitrate, sodium nitroprusside, 3-morpholinosydnonimine, molsidnomine, S-nitroso-N-acetylpenicillamine, S-nitrosoglutathione, N-hydroxyl-L-arginine, S,S-dinitrosodthiol, and NO gas.

ACE inhibitors include benzazapine compounds such as benazepril, and libenzapril; 6H-pyridazino[1,2-α]diazepine derivatives such as cilazapril; 2,3-dihydro-1H-indene compounds such as delapril; L-proline derivatives such as alacepril, captopril, ceronapril, enalapril, fosinopril, lisinopril, moveltipril and spirapril; oxoimidazoline derivatives such as imidapril; 1,4-dihydropyridine compounds such as lacidipine; iso-quinoline carboxylic acid derivatives such as moexipril and quinapril; 1H-indole carboxylic acid derivatives such as pentopril and perindopril; hexahydroindole carboxylic acid derivatives such as trandolapril; cyclopenta[b]pyrrole carboxylic acid derivatives such as ramipril; and 1,4-thiazepine compounds such as temocapril.

Angiotensin-II receptor antagonists useful as anti-pressor agents in the method of this invention include eprosartan, irbesartan, losartan, and valsartan.

$\alpha_1$-Adrenergic receptor antagonists include substituted phenyl derivatives such as midrodrine, phenoxybenzamine, tamsulosin; substituted naphthyl derivatives such as naphazoline; aminoquinazoline derivatives such as alfuzosin, bunazosin, doxazosin, prazosin, terazosin and trimazosin; benzamide compounds such as labetolol; carbazole derivatives such as carvedilol; dimethyluracil derivatives such as urapidil; imidazolidinyl derivatives such as apraclonidine, clonidine; dihydroimidazole derivatives such as phentolamine; indole derivatives such as indoramin; and 1,2,4-triazolo[4,3-a]pyridine compounds such as dapiprazole.

Calcium channel blockers include benzothiazepine compounds such as diltiazem; dihydropyridine compounds such as nicardipine, nifedipine, and nimopidine; phenylalkylamine compounds such as verapamil; diarylaminopropylamine ether compounds such as bepridil; and benimidazole-substituted tetralin compounds such as mibrefadil.

Phosphodiesterase inhibitors include bipyridone compounds such as amrinone; and dihydropyrazolopyrimidine compounds such as sildenafil. Sildenafil functions as a selective type-5 (i.e. c-GMP specific) phosphodiesterase inhibitor, and acts to decrease the metabolism of c-GMP, the second messenger in nitric oxide mediated erectile response. An oral formulation of this medication has proven to be safe and effective in improving erectile duration and rigidity. In females, nitric oxide/NOS exists in human vaginal and clitoral tissue. Sildenafil, alone or in combination with other vasoactive agents, is effective for the long term management of sexual dysfunction for the treatment of vasculogenic male or female sexual dysfunction.

Pharmaceutical Compositions

Pharmaceutical compositions which are useful in the method of the present invention comprise one or more compounds defined above formulated together with one or more non-toxic pharmaceutically acceptable carriers. The pharmaceutical compositions may be specially formulated for oral administration in solid or liquid form, for parenteral injection, or for vaginal or rectal administration. The formulations may, for example, contain a single therapeutic agent selected from ACE inhibitors, angiotensin-1 ($AT_1$) receptor antagonists, $\alpha_1$-adrenoreceptor antagonists, β-adrenergic receptor antagonists, direct-acting vasodilators, NO donors, calcium channel blockers, phosphodiesterase inhibitors, or a combination of two or more agents selected from the same or different therapeutic categories. Moreover, a combination of one or more therapeutic agents from the groups listed above may be combined with a diuretic agent of the class well known in the art.

To enhance delivery to genital vasculature, combined systemic delivery with topical administration of an erectogenic initiator is also contemplated within the scope of this invention. In this manner the anti-pressor drug is delivered to target regions at a markedly enhanced rate. Since prostaglandin-$E_1$ acts both as an anti-pressor and as a direct sexual response initiator, one or more therapeutic agents from the groups listed above can be administered in combination therapy with prostaglandin $PGE_1$. The co-administered $PGE_1$ may be administered by any of the routes discussed below, with topical application being a preferred route.

The pharmaceutical compositions of this invention can be administered to either systemically or locally to humans and other animals. Systemic routes include oral, parenteral, intracisternal, intraperitoneal, trans-cutaneous (by injection or patch), buccal, sub-lingual administration, or by means of an oral or nasal spray. The term "parenteral" administration as used herein refers to modes of administration which include intravenous, intramuscular, intraperitoneal, intrasternal, subcutaneous and intraarterial injection and infusion. Local administration routes include vaginal, rectal, intraurethral, trans-urethral, by intra-cavernosal injection, or topical administration.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous careers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various and bacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug it is desirable to slow the release or absorption of the drug following subcutaneous or intramuscular rejection. This may be accomplished by the use of a liquid suspension of crystalline or amorphous material with low water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(othoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and 1) lubricants such as talc, calcium stearate, magnesium stearate, solid polyethylene glycols, sodium lauryl sulfate, and mixtures thereof. In the case, of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Compositions for rectal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum and release the active compound, Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods for the formation of liposomes are known in the art. See, for example, Prescott, Ed., Methods in Cell Biology, Volume XIV Academic Press, New York, N.Y. (1976), p. 33 et seq.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is well known within the medical art to determine the proper dose for a particular patient by the "dose titration" method. In this method, the patient is started with a dose of the drug compound at a level lower than that required to achieve the desired therapeutic effect. The dose is then gradually increased until the desired effect is achieved. Starting dosage levels for an already commercially available therapeutic agent of the classes discussed above can be derived from the information already available on the dosages employed for the use of the compound as an antihypertensive agent. In a chronic, or long-term dosing regimen to remodel the vasculature in the genitalia and in vascular beds feeding the genitalia, lower doses ranging between about 1/20 to about 1/2 the doses normally given to combat hypertension are used. In short term, acute, or "burst-mode" therapy, the compounds are administered in doses ranging between 1 to 3 times the amounts generally prescribed for hypertension. In these situations, however, appropriate precautions should be taken by the attending physician to closely monitor untoward side-effects peculiar to each particular therapeutic agent.

For the preferred therapeutic agents in the method of the present invention, namely ACE inhibitors, generally dosage levels of about 1 mg to about 300 mg, more preferably of about 5 mg to about 150 mg of active compound per kilogram of body weight per day are administered orally to a patient, with the dose levels appropriately adjusted if the route of administration is other than oral. If desired, the effective daily dose may be divided into multiple doses for purposes of administration, e.g. two to four separate doses per day.

Biological Data

A. Demonstration that the Sex Organs are Not Protected from Pathological Vascular Degradative Modeling 1. Methodology Male spontaneously hypertensive (SH) rats weighing between 246–313 g, and normotensive Sprague-Dawley (SD) rats weighing between 246–440 g were obtained from Charles River Laboratories (Montreal, Quebec, Canada). The animals were maintained in individual cages with a 12 hour light/12 hour dark cycle, and a room temperature of 22–24° C. They were provided with standard rodent chow and tap water ad libitum and were acclimated to the room for at least two days before the experiments. All procedures were carried out in accordance with the guidelines set out by the Canadian Council on Animal Care.

2. Penile Vascular Resistance Properties

Figure 1:
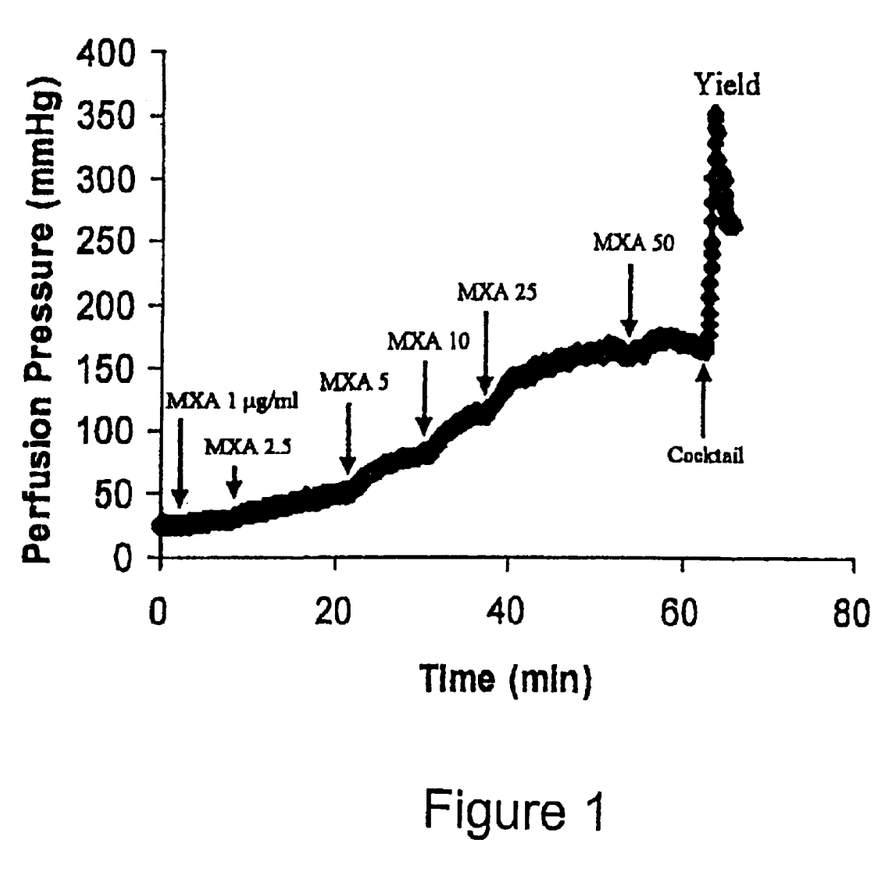
FIG. 1 is a representative cumulative $\alpha_1$-adrenoreceptor concentration-response curve for administration of several doses of methoxamine (MXA) to a spontaneously hypertensive rat. Arrows indicate the point of drug delivery to the penile vascular bed at the concentrations labeled in the Figure. Each concentration of MXA was infused for a period of ten minutes, at which time a plateau was reached. The point marked "yield" in the Figure represents the pressure at maximum constriction of the blood vessels in the vascular bed. This maximum constriction was achieved by administration of a "cocktail" containing a mixture of vasopressin (20 $\mu$g/mL), angiotensin-II (200 $\mu$g/mL), and methoxamine (64 $\mu$g/mL).
Figure 2A:
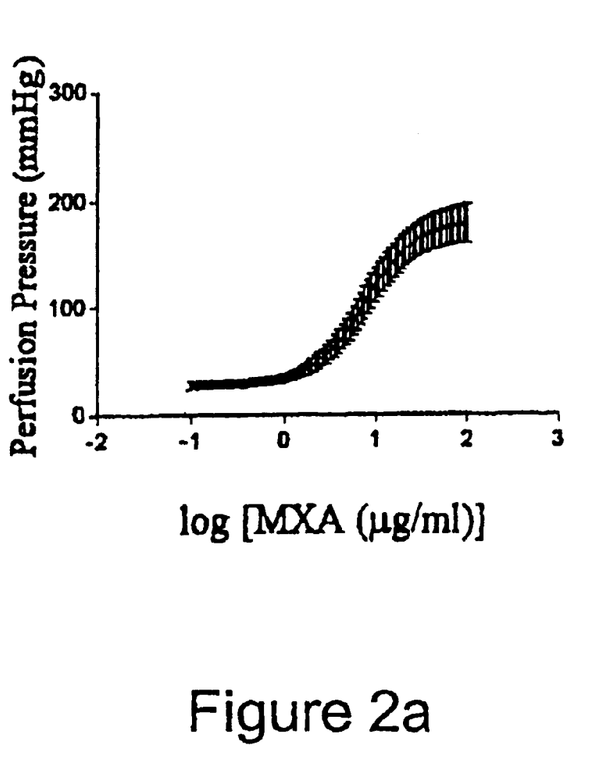
FIGS. 2a–2d shows the average $\alpha_1$-adrenoreceptor concentration-response curves for administration of methoxamine (MXA) to both the penile vascular bed and hindlimb vascular bed perfusion preparations of the spontaneous hypertensive rat (SHR) and the normotensive Sprague-Dawley rat (SD).
Figure 2B:
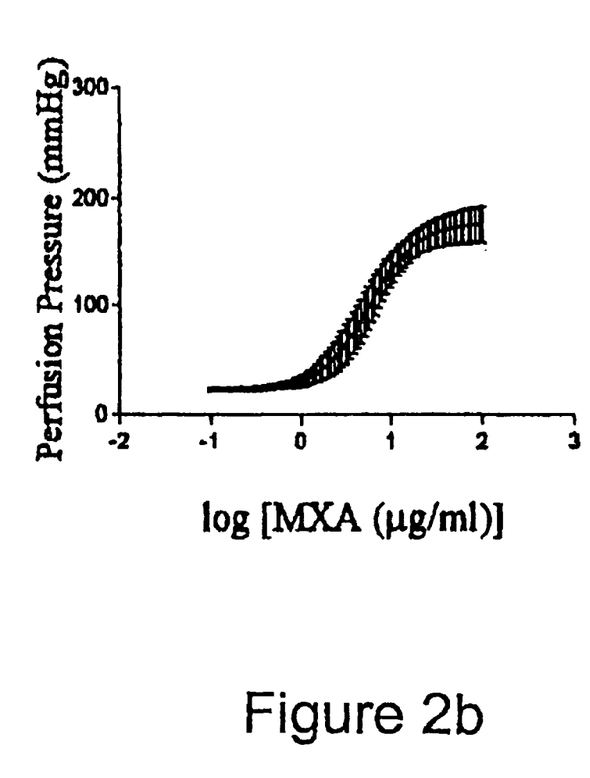
Figure 2C:
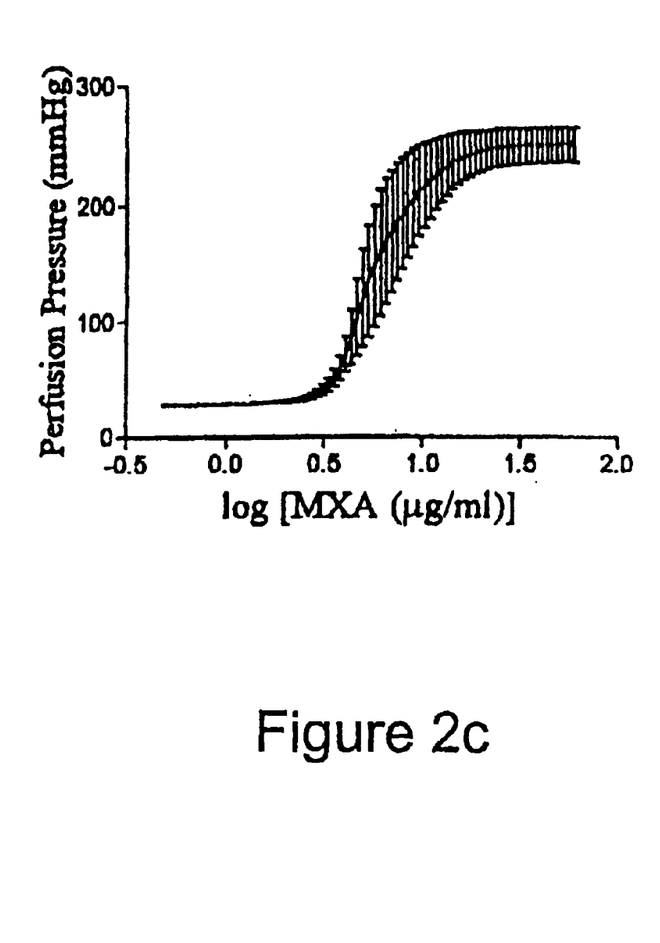
Figure 2D:
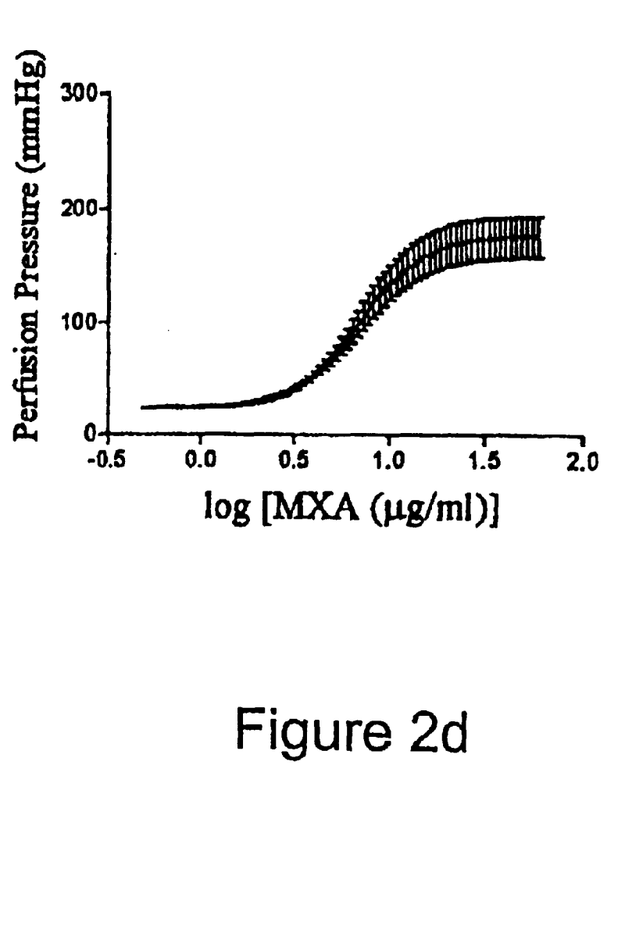

Penile perfusion preparations were made using the procedure established by Banting, J. D., et al., "Isolation and Perfusion of the Pudendal Vasculature in Male Rats. *J Urol.*, 2: 587–590 (1995). A heated chamber served to maintain the ambient temperature and the entire preparation at 37–38° C. The perfusate was held in a reservoir and passed through a heating and a bubble trapping/mixing chamber connected to a single peristaltic pump (Minipuls 2 Pump, Gilson, Inc., 3000 W. Beltline Highway, Middleton, Wis. USA 53562). An injection port was located distal to the pump for the introduction of pharmacological agents to minimize dead volume. Drugs were administered via a Harvard Apparatus, Inc. infusion pump (Harvard Apparatus, Inc., 84 October Hill Road, Holliston, Mass. 01746). The perfusate was a Tyrode-dextran solution consisting of a mixture of 20 mg of KCl, 32.3 mg of $CaCl_2 \cdot H_2O$, 5.1 mg of $MgCl_2 \cdot 6H_2O$, 6.2 mg of $NaH2PO_4 \cdot 2H_2O$, 155 mg of $NaHCO_3$, 100 mg of glucose, and 800 mg of NaCl in each 100 mL of fluid. The solution was maintained at pH 7.4, and a temperature of 37–39° C., and oxygenated with 95% 02 and 5% $CO_2$. The rats were anaesthetized (sodium pentobarbital 60 mg/kg body weight i.p.) and heparinized (1000 IU/kg, i.v.). The bilateral isolation of penile vasculature was achieved by ligating all of the branching arteries except for the pudendal; then the abdominal aorta was cannulated proximal to the iliac bifurcation with a single lumen catheter. The catheter was connected to the perfusion apparatus via a pressure transducer for arterial pressure recording. After sectioning the vena cava and spinal cord to remove venous resistance and to eliminate neural influences, a flow of perfusate (1 mL/min per kg body weight) through the abdominal cannula was initiated. The perfusion pressure was continuously recorded on a data acquisition system (MacLab, AD Instruments, Houston, Tex.). The perfusate was infused for twenty minutes to flush the penile vasculature of blood and obtain a stable pressure before the beginning of any experiment. Following this, sodium nitroprusside (20 µg/mL) was infused to induce maximum vasodilation. The flow rate-perfusion/pressure relationship was determined by measuring the pressure at minimum vascular resistance at flow rates of 0.5, 1.0, 2.0, 4.0 mL/min per kg of body weight. A cumulative $\alpha_1$-adrenoreceptor concentration-response curve to methoxamine (2.5, 5, 10, 25, 50 µg/mL was then generated. Each concentration of methoxamine was infused for a duration of 10 minutes, at which time a plateau was reached. Subsequently, a continuous injection of a cocktail containing a supramaximal concentration of vasoconstrictors (vasopressin, 20.5 µg/mL, angiotensin-II, 200 ng/mL; methoxamine, 64 µg/mL; Sigma, St. Louis, Mo., 63178) was given to ensure that maximum constrictor response that was not dependent upon the activation of a single receptor type was achieved. A second injection of the constrictor cocktail was administered to ensure the tissue "yield" was maximum constriction. This "yield" induced by the multi-vasoconstrictor cocktail has been demonstrated to correlate directly with the bulk of medial vascular smooth muscle cells in the resistance vasculature. A typical perfusion pressure tracing from this protocol can be seen in FIG. 1. At the end of the concentration-response relationship, the aorta was cut distal to the catheter, and a baseline flow-pressure curve was recorded again. This was done to ensure that pressure fell to zero and to account for any false pressure readings that may have resulted due to movement of the catheter during the experiment.

3. Hindlimb Vascular Resistance Properties

The hindlimb perfusion preparation was adopted from a technique originally designed by Folkow et al., *Acta Physiol Scand.*, 80: 93–106 (1973), as modified by Adams et al., *Hypertension*, 14: 191–202 (1989). The perfusion experiment was performed as described above. Drugs were administered into the mixing chamber via a Harvard Apparatus infusion pump. The rats were anaesthetized (Inactin, 100 mg/kg of body weight, i.p.) and heparinized (1000 IU/kg of body weight, i.v.). Following a midline abdominal incision, the abdominal aorta was cannulated proximal to the iliac bifurcation with a double lumen catheter (Storz, St Louis, Mo., USA), and the catheter was extended down the right common iliac artery. One lumen of the catheter was connected to the perfusion apparatus, while the other was connected to a pressure transducer for arterial pressure recording. The rat was perfused at a constant flow rate (2 mL/min per 100 g of body weight) and the experiments were carried out as described above. The flow rate/perfusion pressure relationship was recorded at flow rates of 0.5, 1.0, 2.0, 4.0 mL/min per 100 g of body weight. A cumulative $\alpha_1$-adrenoreceptor concentration-response curve to methoxamine (0.5, 1, 2, 4, 8, 16, 32, 64 µg/mL) was then generated. Each concentration of methoxamine was infused for a duration of 5 minutes, at which time a plateau was reached. Subsequently, a bolus injection of a cocktail containing a supramaximal concentration of vasoconstrictors was given as above. At the end of the concentration-response relationship, the iliac artery was cut distal to the catheter, and the flow pressure curve was monitored again.

Flow rates for the hindlimb perfusion experiments were determined based on expected flow rates of exercising skeletal muscle at maximum dilation. The flow rate used resulted in a perfusion pressure at maximum dilation between 20–25 mm Hg which is well within the expected range. After checking several flow rates in the penile perfusion, a rate was obtained that resulted in a similar perfusion pressure at maximum dilation. The flow rates chosen also allow for the assessment at maximum constriction. This allowed for comparison between strains.

4. Analysis of Data

All values in the figures and tables were expressed as mean ±standard deviation. Results comparing penile and hindlimb vasculature were analyzed using the Student's t-test. Differences were considered as significant at $p<0.05$.

5. Results

There was no significant difference in the body weight of the spontaneously hypertensive rats in the penile assessment group (267±29 g, n=5) and in the hindlimb assessment group (270±5.7 g, n=3). The average body weight of the normotensive Sprague-Dawley rats in the hindlimb assessment group (375±41 g, n=8) was significantly higher than that of the of the normotensive Sprague-Dawley rats in the penile assessment group (284±32 g, n=5). However, this was not considered relevant because in normotensive adult rats there has been shown to be very little correlation between body weight and blood pressure (Adams, M. A., et al., *Hypertension*, 14: 191–202 (1989).

This hemodynamic analysis had similar effects in most parameters between the penile and hindlimb vascular beds within each rat strain. The flow-pressure curve assessed at maximal dilation was similar in both the penile and the hindlimb vasculatures of spontaneously hypertensive and normotensive rats as shown in Table 1. These curves were monitored to ensure a linear increase in perfusion pressure with an increase in flow rate. The increase in the flow rate exerted a radial pressure against the vessel wall and resulted in increased pressure. The spontaneously hypertensive rats trended towards a higher baseline pressure than the normotensive rats. This was observed in both penile and hindlimb vascular beds. These data suggest that spontaneously hypertensive rats may have a smaller lumen thus causing them to operate at a higher pressure than normotensive Sprague-Dawley rats even when there is no constrictor tone on the vessel.

TABLE 1

| Group | Slope Flow Pressure | Maximum Constriction With Methoxamine (mm Hg) | Log $EC_{50}$ | Slope Methoxamine |
|---|---|---|---|---|
| SHR, penile bed | 7.15 ± 2.0 | 172 ± 32 | 0.95 ± 0.19 | 1.64 ± 0.21 |
| SHR, hindlimb bed | 6.68 ± 0.38 | 253 ± 25* | 0.79 ± 0.15 | 5.19 ± 3.0* |
| SD, penile bed | 7.34 ± 2.3 | 171 ± 36 | 0.63 ± 0.24 | 2.03 ± 0.68 |
| SD, hindlimb bed | 6.99 ± 3.4 | 191 ± 55 | 0.78 ± 0.12 | 3.0 ± 0.99 |

*Statistically significant.

Table I shows there was a statistically significant difference in maximum constriction with a supramaximal dose of methoxamine (50 µg/mL for penile and 64 µg/mL for hindlimb vasculature) between spontaneously hypertensive rat hindlimb vasculature (253±25 mmHg) and spontaneously hypertensive rat penile vasculature (172±32 mmHg). This difference was not observed in normotensive Sprague-Dawley rats. The discrepancy is novel and requires further assessment. It is expected that higher responses would be seen in the spontaneously hypertensive rats in both arterial beds, however only the hindlimb vasculature showed a significant difference between spontaneously hypertensive and normotensive rats. Average concentration response curves for methoxamine of the two strains in both beds are shown in FIGS. 2a–2d.

The $EC_{50}$ of the concentration response curve shown in Table 1 gives the concentration of drug at which there is a 50% response to $\alpha_1$-adrenoreceptor stimulation. This value would be an indication of the sensitivity of the tissue to this receptor activation. The logs $EC_{50}$ of the methoxamine concentration-response curves were not different for penile and hindlimb vasculature in both the spontaneously hypertensive and normotensive rats thus indicating similar sensitivity to this receptor stimulation.

The steepest slope of this curve is given in Table 1. In normotensive rats, there was no statistically significant difference in slope between penile vasculature (2.03±0.68) and hindlimb vasculature (3.0±0.99). The parameters showed a statistically significant difference between spontaneously hypertensive rat penile (1.64±0.21) and spontaneously hypertensive rat hindlimb (5.19±3.0). This was expected since the maximal constriction with methoxamine was lower in penile vasculature while the $EC_{50}$, remained the same.

Figure 3A:
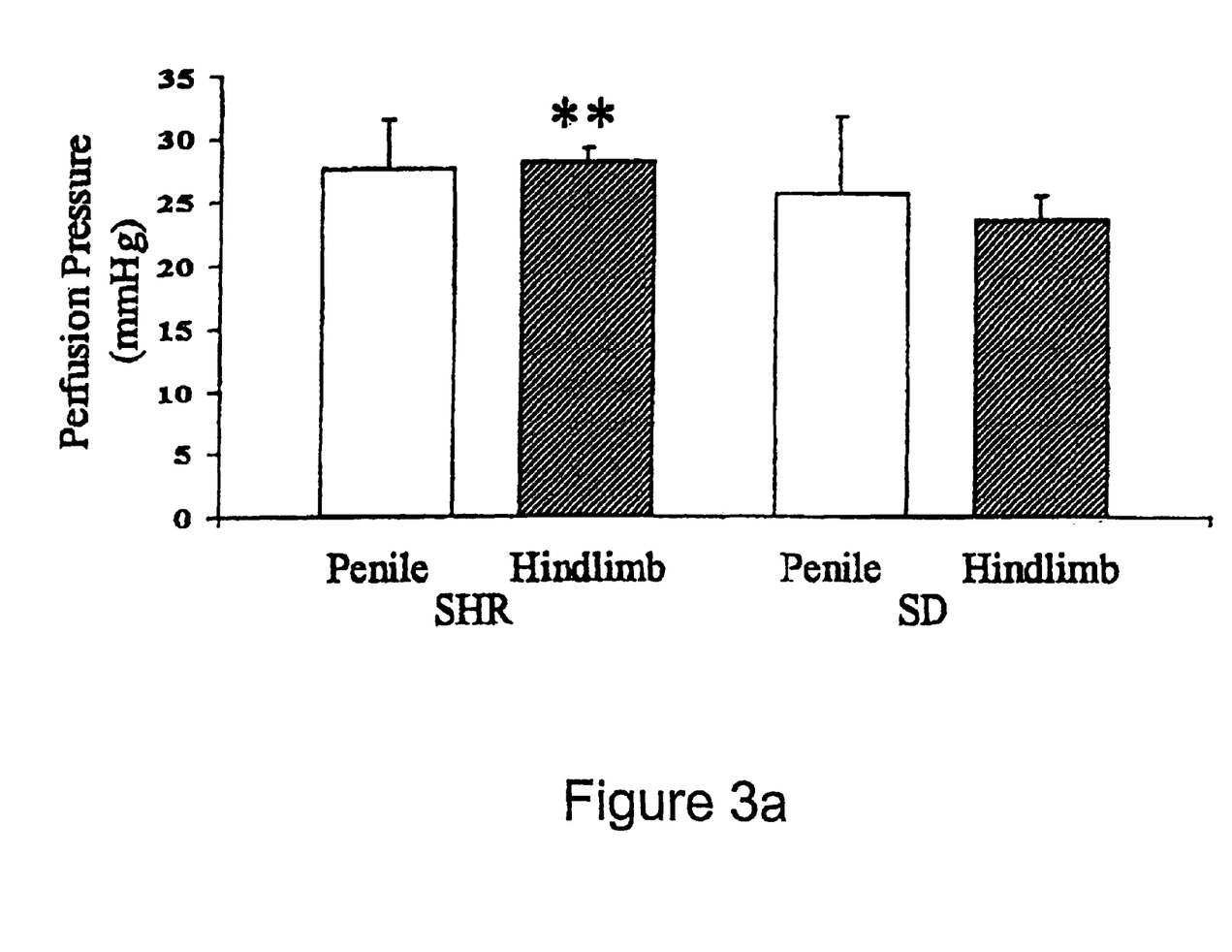
FIG. 3a shows the structurally-based vascular resistance asserted at maximum dilation for the penile and hindlimb perfusion vascular preparations for the spontaneously hypertensive rat (SHR) and the normotensive Sprague-Dawley rat (SD).
Figure 3B:
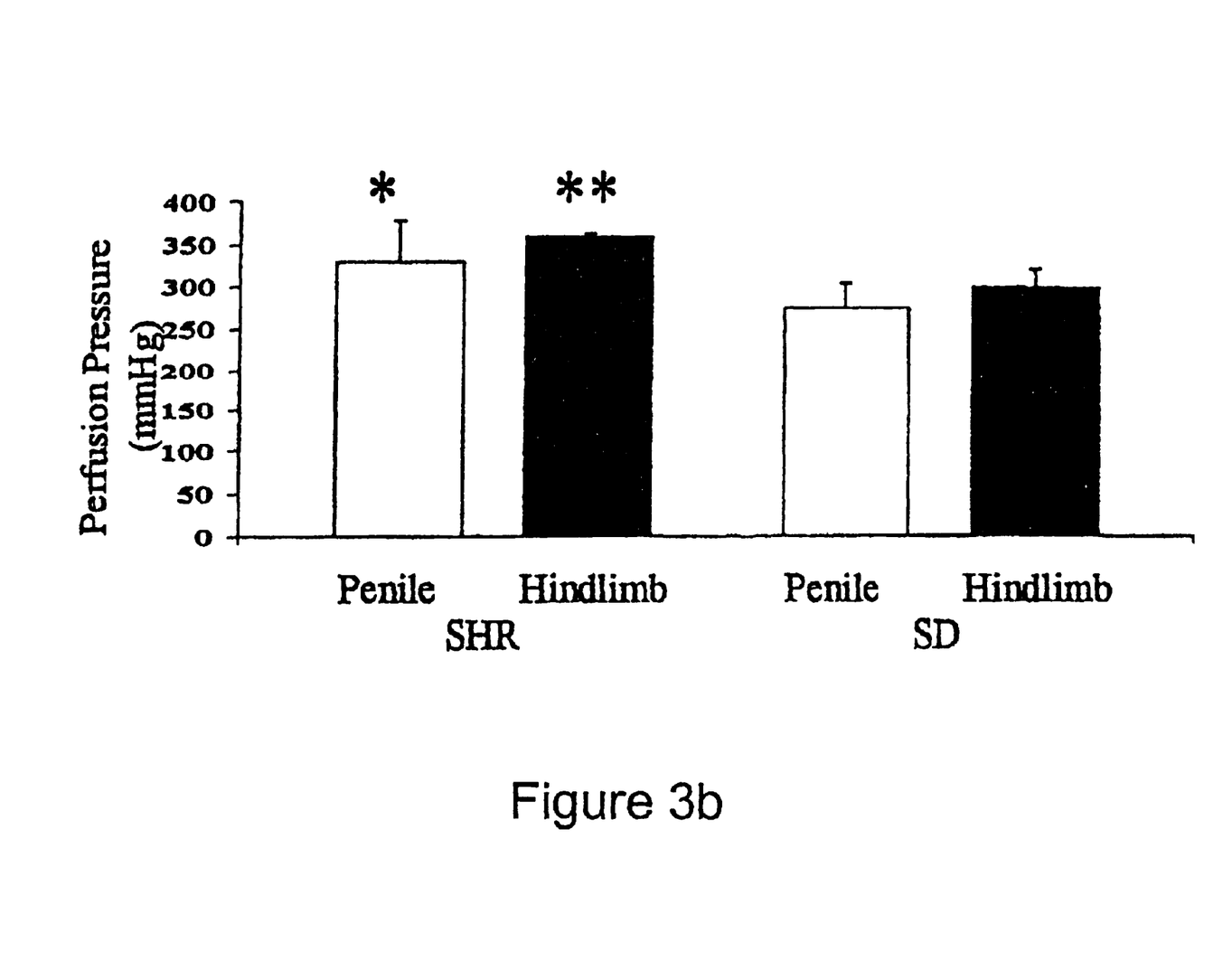
FIG. 3b shows the corresponding structurally-based vascular resistance asserted at maximum constriction for the penile and hindlimb perfusion vascular preparations for the spontaneously hypertensive rat (SHR) and the normotensive Sprague-Dawley rat (SD).

FIG. 3 depicts the structurally-based vascular resistance properties assessed at both maximum dilation and maximum constriction. There was no significant difference in perfusion pressures at maximum dilation within the rat strains. Between the two strains of rats, the penile vasculature trended towards higher pressures in the hypertensive rat as compared to the normotensive Sprague-Dawley rats, however it did not reach a level of significance as in the hindlimb. Spontaneously hypertensive rats reached a point of maximal constriction with a cocktail at a perfusion pressure that was 20% higher than normotensive rats in each vascular bed. There was no statistically significant difference between the two beds within strain, suggesting that the penile and hindlimb vasculature undergo similar structural changes in genetically hypertensive rats. This point demonstrates the increased medial thickening that occurs in the hypertensive rats that allows for the maintenance of higher arterial operating pressures.

6. Discussion

The major findings of the data presented above demonstrate that the penile vasculature is not protected from the structural changes that take place in the other vascular beds of spontaneously hypertensive rats relative to normotensive strains. Increased medial thickening and narrowing of the vascular lumen have been found in blood vessels of a wide range of vascular beds of spontaneously hypertensive rats. Therefore, the overall results of the present series of experiments have shown that the genetic disposition appears to dominate the structure regardless of the vascular bed.

In the present study a hemodynamic methodology was used to compare and contrast structurally-based vascular resistance in two vascular beds. The hindlimb bed was chosen for comparison since the vascular resistance properties are well established and anatomically the feeder vessels of the two beds are common.

These results demonstrate that the resistance properties at maximum dilation were similar in the two beds within strains. A general finding of studies comparing vascular resistance at minimum tone is that a higher perfusion pressure is normally obtained in SHR compared to normotensive rats. Thus, findings of elevated resistance properties at maximum dilation are consistent with there being an overall narrowing of the vascular lumen. Resistance properties were further assessed by determining the slope of the flow-pressure curve at maximum dilation. This relationship was used to determine whether there were any differences in the passive vascular wall elements such as the extracellular matrix components, i.e. if distensibility was altered there would be a differential effect on the flow-pressure curves. Further, a thicker medial wall could also result in a stiffer vessel which would exhibit less compliance with increasing flow. The lack of difference in all of these values suggests that there has been no differential change in the components of the vessel wall within the penile vasculature.

Assessment of the active components of the vessel walls was determined by inducing a state of maximal vasoconstrictor tone using a cocktail of vasoconstrictor agonists. The supramaximal, multiple agonist stimulus produces a maximum constrictor response which is independent of individual receptor population changes thereby reflecting only the overall contractile bulk of the medial smooth muscle cells.

Figure 4:
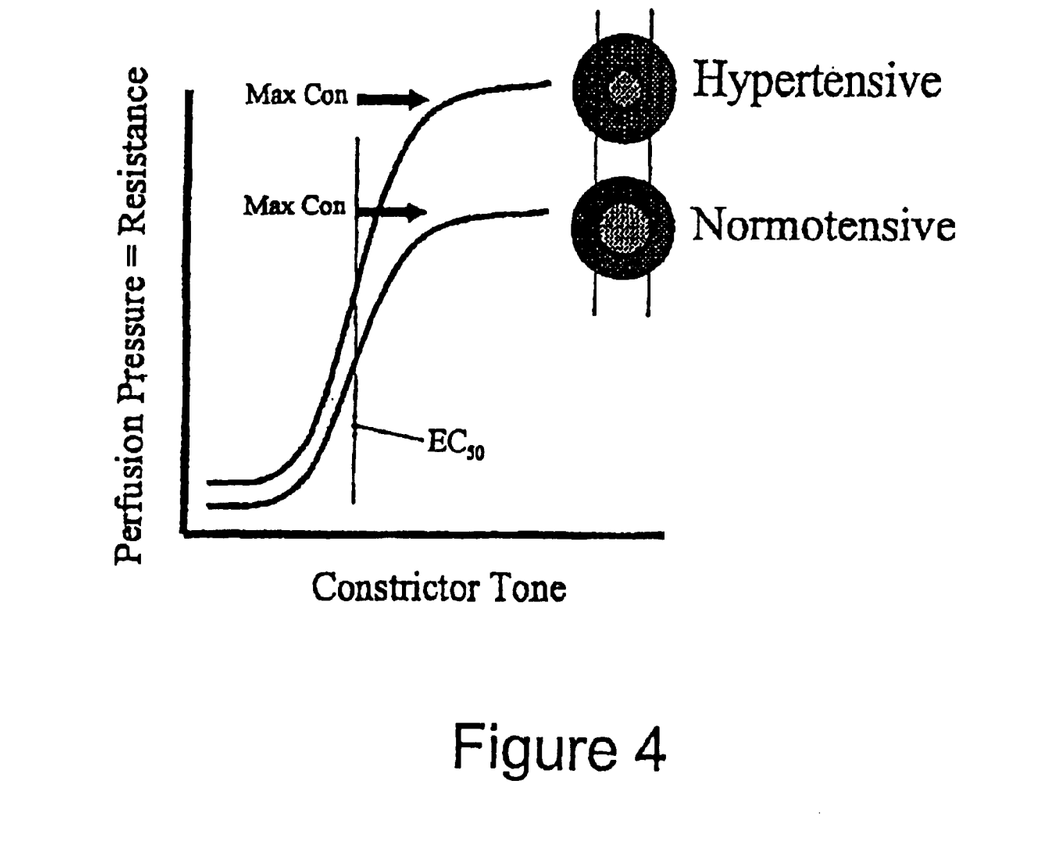
FIG. 4 is a schematic representation depicting structural differences in blood vessels in the spontaneously hypertensive rat (SHR) and the normotensive Sprague-Dawley rat (SD) and the expected impact on resistance to blood flow.

The findings that sensitivity ($EC_{50}$) and reactivity (slope) to $\alpha_1$-adrenoreceptor stimulation were not different between vascular beds or strains likely indicates that there is a similar stimulus-response coupling of the noradrenergic innervation in all of these vessels; i.e. there is a consensus of normal vascular biology. In the schematic diagram of FIG. 4, the concept of structural changes dominating function is depicted. Thus, the curves show that, at any given level of vasoconstrictor tone, the hypertensive circulation will always have increased vascular resistance compared to normotensive circulation. Another way of looking at this concept would be that at the same level of constrictor tone, the normotensive circulation would be able to achieve the same inflow at a proportionately lower perfusion pressure than the hypertensive circulation.

Taken together, the findings indicate that the penile vasculature has an increased average medial mass coupled with decreased average lumen. The generation of an erection is based on the flow when vessels are in a dilated state. Although there was a significant difference in the perfusion pressure at maximum dilation in the hindlimb vasculature of spontaneously hypertensive rats (SHR) when compared to the normotensive Sprague-Dawley (SD) rats, this was not detected in the penile vascular bed. There was however a trend toward significance which may be seen in future studies when animals are used that are genetically closer to the spontaneously hypertensive rat, such as the Wistar-Kyoto rat (Taconic, 273 Hover Avenue, Germantown, N.Y. 12526) which is a more appropriate normotensive control. The penile vasculature is more complex than that of the hindlimb and therefore it may be that differences at maximum dilation are more difficult to detect. It is also unknown whether the size of the penis differs between the strains examined in this study. The length of the vessels changes baseline resistance more than the maximum constriction response because the maximum dilation is flow-dependent, as there is no constrictor tone on the vessel. In contrast, maximum constriction responses are based on the bulk muscular tissue. Therefore although the point of maximum dilation is expected to be higher in the penile vasculature of SHR as compared to a normotensive control it may not be detectable using the Sprague-Dawley rats as a comparison based on the suspected differences between the strains.

B. Therapeutically-Induced Vascular Remodeling in Penile Vasculature

1. Methodology

Adult spontaneously hypertensive rats (SHR) were treated for 1 or two weeks with either enalapril (30 mg/kg of body weight per day) or hydralazine (45 mg/kg of body weight per day). Following this treatment, structurally-based resistance to blood flow in the perfused penile vascular bed and hindlimb vascular bed models were measured using the methods detailed above. Cumulative $\alpha_1$-adrenoreceptor concentration-response curves in response to methoxamine were measured as described above, and the "yield" point determined, following the achievement of maximal vasoconstriction using the vasopressin, angiotensin-11, methoxamine cocktail described above. The animal hearts were excised and weighed. The data are presented in Table 2 below.

TABLE 2

| Group | Slope Flow Pressure | Maximum Constriction With Cocktail "Yield" (mm Hg) | Log EC$_{50}$ | Left Ventricle Weight (g)/ Body Weight (kg) Ratio |
|---|---|---|---|---|
| SHR-E$_2$[1] (n = 7) | 6.45 ± 1.31 | 335 ± 23 | 8.73 ± 0.26 | 2.13 ± 0.08 |
| SHR-E$_1$[1] (n = 5) | 6.10 ± 1.5 | 358 ± 20 | 7.33 ± 1.39 | 2.17 ± 0.05 |
| SHR-H[2] (n = 7) | 6.63 ± 0.86 | 353 ± 11 | 13.56 ± 5 | 2.37 ± 0.12 |
| Control (n = 9) | 7.13 ± 0.63 | 381 ± 21 | 11.95 ± 5.51 | 2.46 ± 0.08 |

[1]Enalapril-treated animals.
[2]Hydralazine-treated animals

The data appearing in Table 2 show that enalapril treatment progressively regressed (remodeled) cardiac and pudendal vascular structure over the 2-week period of treatment. The "yield" value decreased on average by 12.1%±6.0%, while left ventricular mass decreased by 13.6%±3.2%. Hydralazine treatment was somewhat less effective, decreasing the "yield" point by 7.3%±2.9%, and had no significant effect on left ventricular weight (decreased of 3.7%±5.0%).

While there have been shown and described what are believed at present to be the preferred embodiments of the present invention, it will be obvious to those of ordinary skill in the art that various modifications can be made in the preferred embodiments without departing from the scope of the invention as it is defined by the appended claims.

We claim:

1. A method of ameliorating, inhibiting or reversing pathogenic vascular degradative modeling in the iliohypogastric-pudendal arterial bed and genitalia comprising administering to a human patient in need of such treatment a therapeutically effective amount of an anti-pressor agent.

2. The method according to claim 1 wherein said anti-pressor agent comprises one or more compounds selected independently from the group consisting of prostaglandin-E$_1$, ACE inhibitors, AT$_1$-receptor antagonists, $\alpha_1$-adrenergic receptor antagonists, $\beta$-adrenergic receptor antagonists, calcium channel blockers, direct acting vasodilators, NO donors, activators of guanylyl cyclase, activators of adenyl cyclase, and phosphodiesterase inhibitors.

3. The method of claim 2 wherein said anti-pressor agent is an activator of guanylyl cyclase or adenyl cyclase selected from the group consisting of YC-1 and forskolin.

4. The method of claim 2 wherein said anti-pressor agent is a direct acting vasodilator selected from the group consisting of hydralazine and NO donors.

5. The method of claim 4 wherein said NO donor is selected from the group consisting of glyceryl trinitrate, isosorbide 5-mononitrate, isosorbide dinitrate, pentaerythritol tetranitrate, sodium nitroprusside, 3-morpholinosydnonimine, molsidnomine, S-nitroso-N-acetylpenicillamine, 5-nitrosoglutathione, N-hydroxyl-L-arginine, S,S-dinitrosodthiol, and NO gas.

6. The method according to claim 2 wherein said anti-pressor agent is an angiotensin-II receptor antagonists selected from the group consisting of eprosartan, irbesartan, losartan, and valsartan, and mixtures thereof.

7. The method according to claim 2 wherein said anti-pressor agent is an ACE inhibitor selected from the group consisting of alacepril, benazepril, captopril, ceronapril, cilazapril, delapril, enalapril, fosinopril, imidapril, lacidipine, libenzapnl, lisinopril, moexipril, moveltipril, pentopril, perindopril, quinapril, ramipril, spirapril, temocapril, and trandolapril, and mixtures thereof.

8. The method according to claim 2 wherein said anti-pressor agent is an $\alpha$1-adrenergic antagonist selected from the group consisting of alfuzosin, apraclonidine, bunazosin, carvedilol, clonidine, dapiprazole, doxazosin, indoramin, labetolol, midrodrine, naphazoline, phenoxybenzamine, phentolamine, prazosin, tamsulosin, terazosin, trimazosin, and urapidil, and mixtures thereof.

9. The method according to claim 2 wherein said anti-pressor agent is a calciumchannel blocker selected from the group consisting of bepridil, diltiazem, mibrefadil, nicardipine, nifedipine, nimopidine, and verapamil, and mixtures thereof.

10. The method according to claim 2 wherein said anti-pressor agent is a phosphodiesterase inhibitor selected from the group consisting of amrinone and sildenafil.

11. The method according to claim 2 wherein said anti-pressor agent is co-administered with a diuretic compound.

12. The method according to claim 2 wherein said anti-pressor agent is co-administered with prostaglandin-E$_1$.

13. The method of claim 1 wherein said anti-pressor agent is administered to a normotensive patient.

14. The method of claim 1 wherein said anti-pressor agent is administered on a chronic basis at a dose ranging between one-twentieth to one-half the dose normally given to a hypertensive patient.

15. The method of claim 1 wherein said anti-pressor agent is administered for a period ranging between about three days to about twenty-one days at a dose ranging between one to three times the dose normally given to a hypertensive patient.

16. The method according to claim 14 wherein said anti-pressor agent is administered to a normotensive patient.

17. The method according to claim 15 wherein said anti-pressor agent is administered to a normotensive patient.

18. A method of remodeling the vascular bed which supplies blood to the genitalia, comprising administering to a patient in need thereof a therapeutically effective amount of an anti-pressor agent.

19. The method according to claim 18 wherein said anti-pressor agent comprises one or more compounds selected independently from the group consisting of prostaglandin-E$_1$, ACE inhibitors, AT$_1$-receptor antagonists, $\alpha_1$-adrenergic receptor antagonists, $\beta$-adrenergic receptor antagonists, calcium channel blockers, direct acting vasodilators, NO donors, activators of guanylyl cyclase, activators of adenyl cyclase, and phosphodiesterase inhibitors.

20. The method of claim 19 wherein said anti-pressor agent is an activator of guanylyl cyclase or adenyl cyclase selected from the group consisting of YC-1 and forskolin.

21. The method of claim 19 wherein said anti-pressor agent is a direct acting vasodilator selected from the group consisting of hydralazine and NO donors.

22. The method of claim 21 wherein said NO donor is selected from the group consisting of glyceryl trinitrate, isosorbide 5-mononitrate, isosorbide dinitrate, pentaerythritol tetranitrate, sodium nitroprusside, 3-morpholinosydnonimine, molsidnomine, S-nitroso-N-acetylpenicillamine, S-nitrosoglutathione, N-hydroxyl-L-arginine, S,S-dinitrosodthiol, and NO gas.

23. The method according to claim 19 wherein said anti-pressor agent is an angiotensin-II receptor antagonists selected from the group consisting of eprosartan, irbesartan, losartan, and valsartan, and mixtures thereof.

24. The method according to claim 19 wherein said anti-pressor agent is and ACE inhibitor selected from the group consisting of alacepril, benazepril, captopril, ceronapril, cilazapril, delapril, enalapril, fosinopril, imidapril, lacidipine, libenzapril, lisinopril, moexipril, nioveltipril, pentopril, perindopril, quinapril, ramipril, spirapril, temocapril, and trandolapril, and mixtures thereof.

25. The method according to claim 19 wherein said anti-pressor agent is an α1-adrenergic antagonist selected from the group consisting of alfuzosin, apraclonidine, bunazosin, carvedilol, clonidine, dapiprazole, doxazosin, indoramin, labetolol, midrodrine, naphazoline, phenoxybenzainine, phentolamine, prazosin, tamsulosin, terazosin, trimazosin, and urapidil, and mixtures thereof.

26. The method according to claim 19 wherein said anti-pressor agent is a calcium channel blocker selected from the group consisting of bepridil, diltiazem, mibrefadil, nicardipine, nifedipine, nimopidine, and verapamil, and mixtures thereof.

27. The method according to claim 19 wherein said anti-pressor agent is a phosphodiesterase inhibitor selected from the group consisting of amrinone and sildenafil.

28. The method according to claim 19 wherein said anti-pressor compound is co-administered with a diuretic agent.

29. The method according to claim 19 wherein said anti-pressor compound is co-administered with prostaglandin-$E_1$.

30. The method of claim 18 wherein said anti-pressor agent is administered on a chronic basis at a dose ranging between one-twentieth to one-half the dose normally given to hypertensive patient.

31. The method of claim 18 wherein said anti-pressor agent is administered for a period ranging between about three days to about twenty-one days at a dose ranging between one to three times the dose normally given to a hypertensive patient.

32. The method according to claim 30 wherein said anti-pressor agent is administered to a normotensive patient.

33. The method according to claim 31 wherein said anti-pressor agent is administered to a normotensive patient.

* * * * *

UNITED STATES PATENT AND TRADEMARK OFFICE
CERTIFICATE OF CORRECTION

PATENT NO. : 6,787,553 B2  Page 1 of 1
DATED : September 7, 2004
INVENTOR(S) : Adams et al.

It is certified that error appears in the above-identified patent and that said Letters Patent is hereby corrected as shown below:

Column 16,
Line 9, replace "libenzapnl" with -- libenzapril --.
Line 20, replace "calciumchannel" with -- calcium channel --.

Column 17,
Line 14, replace "nioveltipril" with -- moveltipril --.

Signed and Sealed this

Second Day of August, 2005

JON W. DUDAS
*Director of the United States Patent and Trademark Office*